United States Patent [19]

Mizukami et al.

[11] Patent Number: 4,927,758

[45] Date of Patent: May 22, 1990

[54] PROCESS FOR PRODUCING HISTIDINE

[75] Inventors: Toru Mizukami; Ryoichi Katsumata, both of Machida; Tetsuo Oka, Yokohama, all of Japan

[73] Assignee: Kyowa Hakko Kogyo Co., Ltd., Tokyo, Japan

[21] Appl. No.: 89,922

[22] Filed: Aug. 25, 1987

Related U.S. Application Data

[63] Continuation of Ser. No. 580,814, Feb. 16, 1984.

[30] Foreign Application Priority Data

Feb. 17, 1983 [JP] Japan ................... 58-25397

[51] Int. Cl.$^5$ .................... C12R 13/24; C12N 1/20; C12P 1/13; C12P 1/15
[52] U.S. Cl. .................... 435/107; 435/252.32; 435/840; 435/843; 935/60
[58] Field of Search ............ 435/107, 172.3, 252.32, 435/320, 840, 843; 935/29, 23, 60, 73

[56] References Cited

U.S. PATENT DOCUMENTS

| | | | |
|---|---|---|---|
| 3,713,977 | 1/1973 | Nakayama et al. | 435/107 |
| 4,495,283 | 1/1985 | Araki | 435/107 |
| 4,601,983 | 7/1986 | Nakamori | 435/115 |

FOREIGN PATENT DOCUMENTS

| | | | |
|---|---|---|---|
| 0553843 | of 0000 | Australia . | |
| 0058889 | 9/1982 | European Pat. Off. | 935/29 |
| 0063763 | 11/1982 | European Pat. Off. | 435/843 |
| 0066129 | 12/1982 | European Pat. Off. . | |
| 0071023 | 2/1983 | European Pat. Off. . | |
| 0082485 | 6/1983 | European Pat. Off. . | |
| 0088166 | 9/1983 | European Pat. Off. . | |
| 0093611 | 11/1983 | European Pat. Off. . | |
| 01311171 | 1/1985 | European Pat. Off. . | |
| 0062983 | 4/1985 | Japan | 435/107 |
| 2055805 | 3/1981 | United Kingdom | 435/107 |
| 2076853 | 12/1981 | United Kingdom . | |

OTHER PUBLICATIONS

Brenner and Ames, The Metabolic Pathway, 3rd Ed., vol. 5 (1971), 349.85.
Genetics, vol. 66 (1970), 231.44.
P.N.A.S, vol. 70, No. 9 (1973), 2692:6.

*Primary Examiner*—Jayme A. Huleatt
*Attorney, Agent, or Firm*—Fitzpatrick, Cella, Harper & Scinto

[57] ABSTRACT

Disclosed is a process for producing histidine by transforming a host microorganism belonging to the genus Corynebacterium or Brevibacterium with a recombinant DNA of a DNA fragment containing a gene involved in the biosynthesis of histidine and a vector DNA, culturing the transformant in a nutrient medium, accumulating histidine in the culture medium and recovering histidine therefrom.

9 Claims, No Drawings

PROCESS FOR PRODUCING HISTIDINE

This application is a continuation of application Ser. No. 580,814 filed Feb. 16, 1984, now abandoned.

BACKGROUND OF THE INVENTION

For the direct production of histidine by fermentation, methods using mutant strains resistant to histidine analog of the bacteria belonging to the genus Corynebacterium, Brevibacterium, Serratia, and the like are known.

No example of expressing a desired gene in a host microorganism belonging to the genus Corynebacterium of Brevibacterium by introducing a recombinant DNA containing such desired gene and vector, one of which is foreign to a host microorganism, into such host microorganism has been reported. In the recombinant DNA technology using a microorganism belonging to the genus Corynebacterium or Brevibacterium as a host, it is necessary to construct vectors autonomously replicable in these microorganisms, having selectable markers and useful for cloning of desired genes, and to establish an efficient transformation system. Furthermore, methods to overcome various barriers against the expression of foreign recombinant DNA will be necessary.

The present inventors have constructed plasmid vectors autonomously replicable in a microorganism belonging to the genus Corynebacterium or Brevibacterium and having selectable markers and adequate cloning sites and have developed a highly efficient transformation system (Japanese Published Unexamined Patent Application Nos. 183799/82, 186492/82, 186489/82 and 105999/83). Further, the present inventors have found that the plasmid vectors are useful for expressing a foreign gene in a host microorganism and increasing the productivity of amino acids by ligating a DNA fragment containing a foreign gene involved in the biosynthesis of amino acids such as glutamic acid and lysine to the plasmid vectors according to the procedures in recombinant DNA technology (U.S. Pat. No. 4,237,224 and Methods in Enzymology 68, Recombinant DNA, edited by Ray Wu, Academic Press 1979) and transforming *Corynebacterium glutamicum* L-22 or its derivatives using the transformation methods described in Japanese Patent Application No. 211908/81.

Furthermore, the present inventors have found that a microorganism prepared by the same method has acquired an increased productivity of histidine.

SUMMARY OF THE INVENTION

This invention relates to a process for producing histidine by a novel expression method of a gene. More specifically, the present invention is a process for producing histidine by transforming a host microorganism belonging to the genus Corynebacterium or Brevibacterium with a recombinant DNA of a DNA fragment containing a gene involved in the biosynthesis of histidine and a vector DNA, culturing the transformant in a nutrient medium, accumulating histidine in the culture medium and recovering histidine therefrom.

DESCRIPTION OF THE INVENTION

The present invention provides a process for producing histidine by cultivating in a medium a transformant which is obtained by transforming a microorganism belonging to the genus Corynebacterium or Brevibacterium with a recombinant DNA or a DNA fragment containing a gene involved in the biosynthesis of histidine and a vector DNA.

As the DNA fragment containing the gene used in the present invention, the DNA fragment containing a gene involved in the biosynthesis of histidine derived from eukaryotes, prokaryotes, viruses, bacteriophages or plasmids is used. As the gene derived from prokaryotes, the gene derived from a bacterium belonging to the genus Escherichia, Corynebacterium, Brevibacterium, Bacillus, Staphylococcus or Serratia and responsible for the biosynthesis of histidine or the metabolism relating to the biosynthesis is preferably used.

Specifically, the gene which is used is responsible for the synthesis of ATP phosphoribosyl transferase, i.e., the first enzyme in the pathway of controlling histidine biosynthesis. As the DNA fragment containing a gene involved in the biosynthesis of histidine in *Escherichia coli*, a histidine operon which contains, in order, hisG, hisD, hisC, hisB, hisH, hisA, hisF, hisI and hisE, is known [Brenner, M. and Ames, B. N., The Metabolic Pathway, 3rd. Ed. Vol. 5, Vogel, H. J. (ed.) Academic Press P. 349 (1971)]. The gene responsible for the synthesis of ATP phosphoribosyl transferase is the hisG gene. Therefore, hisG gene derived from *Escherichia coli* or a gene which has the same function as hisG gene and is derived from a bacteria, such as, *Corynebacterium glutamicum*, is preferably used.

The vector used in the present invention should autonomously replicate in cells of the host microorganism. Preferably, plasmids isolated from microorganisms belonging to the genus Corynebacterium by the present inventors or derivatives thereof such as pCG1 (Japanese Published Unexamined Patent Application No. 134500/82), pCG2 (Japanese Published Unexamined Patent Application No. 35197/83), pCG4 (Japanese Published Unexamined Patent Application No. 183799/82), pCE54, pCG11 and pCB101 are used. Microorganisms carrying the following plasmids have been deposited with the Fermentation Research Institute, Agency of Industrial Science and Technology, Ibaraki, Japan and the American Type Culture Collection, Rockville, Md., U.S.A. under the following accession numbers.

| Plasmid | FERM P- | ATCC |
|---------|---------|------|
| pCG1    | 5865    | 31808 |
| pCG2    | 5954    | 31832 |
| pCG4    | 5939    | 31830 |
| pCE54   | —       | 39019 |
| pCG11   | —       | 39022 |
| pCB101  | —       | 39020 |

Of the foregoing plasmids, pCG11 is most preferred.

Plasmid pCG11 is a plasmid constructed by the present inventors and descrived in Japanese Published Unexamined Patent Application No. 134500/82 and U.S. patent application Ser. No. 346,867. Plasmid pCG11 is prepared by inserting the BamHI fragment containing a gene responsible for resistance to streptomycin and/or spectinomycin (referred to as $Sm^R/Spec^R$ gene hereinafter) of plasmid pCG4 isolated from *Corynebacterium glutamicum* 225-250 (ATCC 31830, FERM P-5939) into the unique BglII cleavage site of plasmid pCG1 isolated from *Corynebacterium glutamicum* 225-57 (ATCC 31808, FERM P-5865) using the same cohesive ends of both fragments.

Transformation with the ligated DNA mixture is carried out using protoplasts of the genus Corynebacterium or Brevibacterium, and the method described in U.S. patent application Ser. No. 368,034, filed Apr. 13, 1982 and Japanese Published Unexamined Patent Application Nos. 186493/82 and 186489/82. Streptomycin or spectinomycin is used for selection. Transformants are recovered as a colony regenerated on a hypertonic agar medium containing 100–400 µg/ml streptomycin or 200–1000 µg/ml spectinomycin which does not allow the reversion to normal cells of protoplast which are not treated with the ligation mixture. Alternatively, transformants are regenerated unselectively on a regeneration medium, and the resultant cells are scraped and resuspended, followed by the isolation of those cells grown on an agar medium containing a drug in a concentration wherein the recipient normal cells cannot grow, that is, generally 5–50 µg/ml streptomycin, 50–500 µg/ml spectinomycin.

Plasmid DNAs in the transformants can be isolated from cultured cells of the transformants and purified according to the methods described in U.S. patent application Ser. No. 346,867 filed Feb. 8, 1982 now U.S. Pat. No. 4,617,267 and Japanese Published Unexamined Patent Application Nos. 134500/82 and 186489/82. The structures of the DNAs can be determined by digesting them with various restriction endonucleases and analyzing the DNA fragments by agarose gel electrophoresis. The plasmid isolated from one of the transformants is named pCG11. Plasmid pCG11 has a molecular weight of about 6.8 Kb and a single cleavage site for BglII and PstI and gives $Sm^R/Spec^R$ phenotype.

The vector plasmid, pCE53, is prepared by inserting BglII-restricted pCG1 into the BamHI site near the kanamycin-resistance ($Km^R$) gene of pGA22 and ligating them by taking advantage of their common cohesive ends. pCG1 is prepared as described above, while pGA22 is prepared from a strain of Escherichia coli by the method of An, G., et al. J. Bacteriol. 140, 400 (1979)].

Transformation with the DNA mixture is carried out using protoplasts of the genus Corynebacterium or Brevibacterium, and the method described in U.S. patent application Ser. No. 368,034, filed Apr. 13, 1982 now U.S. Pat. No. 4,683,205 and Japanese Published Unexamined Patent Application Nos. 186492/82 and 186489/82. Tetracycline, chloramphenicol or kanamycin is used for selection. Transformants are recovered as a colony regenerated on a hypertonic agar medium containing 0.4–1.6 µg/ml tetracycline (Tc), 2.5–5 µg/ml chloramphenicol (Cm) or 100–800 µg/ml kanamycin (Km) which does not allow the reversion to normal cells of the protoplasts which are not treated with the ligation mixture. Alternatively, transformants are regenerated unselectively on a regeneration medium, and the resultant cells are scraped and suspended, followed by the isolation of those cells grown on an agar medium containing a drug in a concentration wherein the recipient normal cells cannot grow, that is, generally 0.5–4 µg/ml Tc, 2–15 µg/ml Cm or 2–25 µg/ml Km.

Isolation, purification and determination of structure of plasmids are carried out described above. The plasmid isolated from one of the transformants is named pCE53. It has a molecular weight of about 10.9 Kb, has Cm, Km, Tc and amplicillin resistance genes of pGA22 and can replicate in both Escherichia coli and Corynebacterium glutamicum.

Recovery of plasmids from the strains is carried out according to the methods described in U.S. patent applications, Ser. No. 346,867, filed Feb. 8, 1982, Ser. No. 368,035 filed Apr. 13, 1982, now U.S. Pat. No. 4,500,640 and Ser. No. 410,887 filed Aug. 24, 1982, now U.S. Pat. No. 4,489,160 and Japanese Published Unexamined Patent Application Nos. 134500/82 and 183799/82 and Japanese Patent Application No. 133557/81.

Preparation of a recombinant DNA of a vector DNA with a DNA fragment containing a gene is carried out by conventional in vitro recombinant DNA technology, e.g. cleavage and ligation of a donor DNA containing a desired gene to a vector DNA (refer to Japanese Pulished Unexamined Patent Application No. 126789/83, U.S. Pat. No. 4,237,224). DNAs can readily be cleaved with restriction endonucleases.

The ligase reaction gives recombinants containing genes other than the desired gene. The desired recombinant DNA can be obtained by directly transforming a microorganism of the genus Corynebacterium or Brevibacterium with the DNA mixture, selecting the transformants having the phenotype derived from the desired gene and isolating the desired recombinant DNA from the cultured cells of the transformants. Instead of cloning the desired gene directly in a microorganism of the genus Corynebacterium or Brevibacterium, the desired gene can be cloned by using another host-vector system such as Escherichia coli. Then, it is recloned in vitro into a vector of the genus Corynebacterium or Brevibacterium to transform these microorganisms and transformants containing the desired recombinant plasmid are selected as mentioned above.

The following references are helpful for the construction of recombinant DNA:

S. N. Cohen, et al., U.S. Pat. No. 4,237,224;
Idenshi Sosa Jikkenho, edited by Yasuyuki Takagi, printed by Kodansha Scientific (1980);
Method in Enzymology 68, Recombinant DNA edited by Ray Wu, Academic Press, 1979

Microorganisms belonging to the genus Corynebacterium or Brevibacterium and which are competent for incorporating DNAs may be used as the host microorganisms in the present invention. The following are examples of a suitable host microorganism.

|  | Accession Number | |
| --- | --- | --- |
|  | FERM P- | ATCC |
| Corynebacterium glutamicum L-15 | 5946 | 31834 |
| Corynebacterium herculis |  | 13868 |
| Corynebacterium herculis L-103 | 5947 | 31866 |
| Brevibacterium divaricatum L-204 | 5948 | 31867 |
| Brevibacterium lactofermentum |  | 13869 |
| Brevibacterium lactofermentum L-312 | 5949 | 31868 |
| Brevibacterium flavum |  | 14067 |

Transformation of the host microorganisms with recombinant DNAs is carried out by the following steps:

(1) Preparation of protoplasts of host cells;
(2) Transformation of the protoplasts with a recombinant DNA;
(3) Regeneration of the protoplasts to normal cells and selection of a transformant;

These steps are described in detail below.

1. Preparation of protoplasts of host cells:

The preparation of protoplasts is carried out by culturing a microorganism under conditions which render it sensitive to lysozyme, a lytic enzyme, and treating the cultured cells with lysozyme in a hypertonic solution to remove the cell wall. In order to render microbial cells sensitive to lysozyme, reagents inhibiting the synthesis of bacterial cell walls are used. For example, microbial cells sensitive to lysozyme are obtained by adding, during the logarithmic growth phase, an amount of penicillin which does not inhibit or sub-inhibits the growth and then continuing culturing for several generations.

For culturing, any medium wherein the microorganism can grow may be used. For example, a nutrient medium NB (pH 7.2) consisting of 20 g/l powdered bouillon and 5 g/l yeast extract and a semi-synthetic medium SSM (pH 7.2) consisting of 10 g/l glucose, 4 g/l NH$_4$Cl, 2 g/l urea, 1 g/l yeast extract, 1 g/l KH$_2$PO$_4$, 3 g/l K$_2$HPO$_4$, 0.4 g/l MgCl$_2$.6H$_2$O, 10 mg/l FeSO$_4$.7H$_2$O, 0.2 mg/l MnSO$_4$.(4–6)H$_2$O, 0.9 mg/l ZnSO$_4$.7H$_2$O, 0.4 mg.l CuSO$_4$.5H$_2$O, 0.09 mg/l Na$_2$B$_4$O$_7$.10H$_2$O, 0.04 mg/l (NH$_4$)$_6$Mo$_7$O$_{24}$.4H$_2$), 30 $\mu$g/l biotin and 1 mg/l thiamine hydrochloride are used. Microbial cells are inoculated in the medium and culturing is carried out with shaking. The optical density (OD) of the culture medium at 660 nm is monitored with a colorimeter and penicillin, such as penicillin G, is added to the medium at an initial stage of the logarithmic growth phase (OD:0.1–0.4) in a concentration of 0.1 to 2.0 U/ml. Culturing is continued to an OD value of 0.3–0.5, and then cells are harvested and washed with the SSM medium. The washed cells are resuspended in a suitable hypertonic medium such as PFM medium (pH 7.0–8.5) wherein 0.4M sucrose and 0.01M MgCl$_2$.6H$_2$O are added to 2 fold diluted SSM medium, and RCG medium (pH 7.0–8.5) consisting of 5 g/l glucose, 5 g/l casein hydrolysate, 2.5 g/l yeast extract, 3.5 g/l K$_2$HPO$_4$, 1.5 g/l KH$_2$PO$_4$, 0.41 g/l MgCl$_2$.6H$_2$O, 10 mg/l FeSO$_4$.7H$_2$O, 2mg/l MnSO$_4$.(4–6)H$_2$O, 0.9 mg/l ZnSO$_4$.7H$_2$O, 0.4 mg/l CuSO$_4$.5H$_2$O, 0.09 mg/l Na$_2$B$_4$O$_7$.10H$_2$O, 0.04 mg/l (NH$_4$)$_6$Mo$_7$O$_{24}$.4H$_2$O, 30 $\mu$g/l biotin, 2 mg/l thiamine hydrochloride and 135 g/l sodium succinate or RCGP medium which consists of RCG medium and 3% polyvinyl purrolidone. To the cell suspension, lysozyme is added to a final concentration of 0.2 to 10 mg/ml, and the mixture is allowed to react at a temperature of 30° to 37° C. Protoplast formation proceeds with time and is monitored with an optical microscope. The period required for the conversion of most cells to protoplasts depends on the concentrations of the penicillin used for the lysozyme-sensitization and the amount of lysozyme used. The period is 3-24 hours under the conditions mentioned above.

Since protoplasts formed are destroyed under hypotonic conditions, the extent of the formation of protoplast is determined indirectly from the number of normal cells surviving under hypotonic conditions. Generally, the ratio of surviving normal cells are kept below $10^{-4}$ per lysozyme-treated normal cell.

The protoplasts prepared as above have colony-forming (regenerating) ability on a suitable hypertonic agar medium. As a regeneration medium, a nutrient medium, a semi-synthetic medium or a synthetic medium containing various amino acids, which contains 0.3 to 0.8M sodium succinate and 0.5 to 6% polyvinyl pyrrolidone with a molecular weight of 10,000 or 40,000 is preferably used. Generally, a semi-synthetic medium RCGP (pH 7.2) wherein 3% polyvinyl pyrrolidone (molecular weight of 10,000) and 1.4% agar are added to the RCG medium is used. Regeneration is carried out at a temperature of 25° to 35° C. The cultivation time required for the regeneration of protoplasts depends upon the strain used but usually in 10 to 14 days colonies can be picked up. The efficiency of the regeneration of protoplasts on the RCGP medium also depends on the strain used, the concentrations of the penicillin added during the cultivation and the concentration of lysozyme used. The efficiency is generally $10^{-2}$–$10^{-4}$ cells per normal cell treated with lysozyme.

2. Transformation of the protoplasts with a recombinant DNA:

Introduction of a recombinant DNA into the protoplast is carried out by mixing the protoplast and the DNA in a hypertonic solution which protects the protoplast and by adding to the mixture polyethyleneglycol (PEG, average molecular weight: 1,540–6,000) or polyvinylalcohol (PVA, degree of polymerization: 500–1,500) and a divalent metal cation which stimulates the uptake of DNA. As a stabilizing agent for the hypertonic conditions, those generally used to protect protoplasts of other microorganisms such as sucrose and sodium succinate are also employed. PEG and PVA can be used at a final concentration of 5 to 60% and 1 to 20%, respectively. Divalent metal cations such as Ca$^{++}$, Mg$^{++}$, Mn$^{++}$, Ba$^{++}$ and Sr$^{++}$ are effectively used alone or in combination at a final concentration of 1 to 100 mM. Transformation is carried out satisfactorily at 0° to 25° C.

3. Regeneration of the protoplasts to normal cells and selection of a transformant:

Regeneration of the protoplast transformed with a recombinant DNA is carried out in the same way as mentioned above by spreading the protoplast on a hypertonic agar medium such as RCGP medium containing sodium succinate and polyvinyl pyrrolidone and incubating at a temperature wherein normal cells can grow, generally 25° to 35° C. Transformants are obtained by selecting for the phenotype derived from donor DNAs. The selection may be carried out simultaneously with regeneration on a hypertonic agar medium or may be carried out on a hypotonic agar medium after non-selective reversion to normal cells on a hypertonic agar medium.

In the case of the lysozyme-sensitive strains described as the preferred host microorganisms for cloning, the transformation may be carried out by the steps described in (1) to (3) except that the cultured cells are directly treated with lysozyme without prior treatment with penicillin. In that case, transformants are obtained at an efficiency of $10^{-2}$ to $10^{-4}$ per regenerated cell.

The phenotypic expression of the recombinant DNA is carried out by growing the transformant in a conventional nutrient medium. Appropriate reagents may be added to the medium according to the phenotypes expected from the genes on the recombinant DNA.

The thus obtained transformant is cultured in a conventional manner used in the production of histidine by fermentation. That is, the transformant is cultured in a conventional medium containing carbon sources, nitrogen sources, inorganic materials, amino acids, vitamines, etc. under aerobic conditions, with adjustment of temperaure and pH. Histidine, thus accumulated in the medium is recovered.

As the carbon source, various carbohydrates such as glucose, glycerol, fructose, sucrose, maltose, mannose, starch, starch hydrolyzate and molasses, polyalcohols and various organic acids such as pyruvic acid, fumaric acid, lactic acid and acetic acid may be used. According to the assimilability of the microorganism strain used, hydrocarbon and alcohols are employed. Blackstrap molasses is most preferably used.

As the nitrogen source, ammonia, various inorganic or organic ammonium salts such as ammonium chloride, ammonium sulfate, ammonium carbonate and ammonium acetate, urea, and nitrogenous organic substances such as peptone, NZ-amine, meat extract, yeast extract, corn steep liquor, casein hydrolyzate, fish meal or its digested product, defatted soybean or its digested product and chrysalis hydrolyzate are appropriate.

As the inorganic materials, potassium dihydrogenphosphate, dipotassium hydrogenphosphate, ammonium sulfate, ammonium chloride, magnesium sulfate, sodium chloride, ferrous sulfate, manganese sulfate and calcium carbonate may be used. Vitamines and amino acids required for the growth of microorganisms may not be asked, provided that they are supplied with other components mentioned above.

Culturing is carried out under aerobic conditions with shaking or aeration-agitation. Culturing temperature is preferably 20° to 40° C. The pH of the medium during culturing is maintained around neutral. Culturing is continued until a considerable amount of histidine is accumulated, generally for 1 to 5 days.

After completion of the culturing, cells are removed and histidine is recovered from the culture liquor by conventional manners such as treatment with active carbon or ion exchange resin.

Certain specific embodiments of the present invention are illustrated by the following representative examples reflecting actual experimental data.

EXAMPLE 1

Cloning of a gene involved in the biosynthesis of L-histidine derived rom *Corynebacterium glutamicum* C156 strain and production of L-histidine by the expression of the gene in *Corynebacterium glutamicum*, *Corynebacterium herculis*, *Brevibacterium flavum* and *Brevibacterium lactofermentum*:

(1) Preparation of chromosomal DNA of *Corynebacterium glutamicum* C156 and plasmid pCG11:

The chromosomal DNA was prepared from *Corynebacterium glutamicum* C156 L (FERM P-6910 transferred to FERM BP-453) which is resistant to 1,2,4-triazole-3-alanine and capable of producing L-histidine as follows:

A seed culture in NB medium was inoculated into 400 ml of a semi-synthetic medium SSM (pH 7.2) consisting of 20 g/l glucose, 10 g/l $(NH_4)_2SO_4$, 3 g/l urea, 1 g/l yeast extract, 1 g/l $KH_2PO_4$, 0.4 g/l $MgCl_2.6H_2O$, 10 mg/l $FeSO_4.7H_2O$, 0.2 mg/l $MnSO_4.(4-6)H_2O$, 0.9 mg/l $ZnSO_4.7H_2O$, 0.4 mg/l $CuSO_4.5H_2O$, 0.09 mg/l $Na_2B_4O_7.10H_2O$, 0.04 mg/l $(NH_4)_6Mo_7O_{24}.4H_2O$, 30 µg/l biotin and 1 mg/l thiamine hydrochloride. Culturing was carried out with shaking at 30° C. The optical density (OD) at 660 nm was monitored with a Tokyo Koden colorimeter and penicillin G was added to an OD value of 0.2 to a concentration of 0.5 unit/ml. Culturing was continued to an OD value of about 0.6.

Cells were harvested from the culture broth and washed with TES buffer (pH 8.0) consisting of 0.03M tris(hydroxymethyl) aminomethane-HCl (referred to as Tris hereinafter), 0.005M EDTA and 0.05M NaCl. The cells were suspended in a lysozyme solution (pH 8.0) consisting of 12.5% sucrose, 0.1M NaCl, 0.05M Tris and 0.8 mg/ml lysozyme to make 10 ml of a suspension which was allowed to react at 37° C. for 4 hours. High molecular chromosomal DNAs were isolated from the cells by the method of Saito et al., Biochem. Biophys, Acta, 72, 619 (1963).

Separately pCG11 used as a vector plasmid was prepared from *Corynebacterium glutamicum* LA 103/pCG11, ATCC 39022 which is a derivative of *Corynebacterium glutamicum* L-22 and harbors pCG11 as follows.

The strain was grown with shaking at 30° C. in 400 ml of NB medium (pH 7.2) to an OD value of about 0.7. Cells were harvested and washed with TES buffer. The cells were suspended in 10 ml of the aforementioned lysozyme solution and allowed to react at 37° C. for 2 hours. Then 2.4 ml of 5M NaCl, 0.6 ml of 0.5M EDTA (pH 8.5) and 4.4 ml of a solution consisting of 4% sodium lauryl sulfate and 0.7M NaCl were added successively. The mixture was stirred slowly and allowed to stand on an ice water bath for 15 hours. The whole lysate was centrifuged at 4° C. under $69,400 \times g$ for 60 minutes. The supernatant fluid was recovered and 10% (by weight) polyethyleneglycol (PEG) 6,000 (product of Nakarai Kagaku Yakuhin Co.) was added. The mixture was stirred slowly to dissolve completely and then kept on an ice water bath. After 10 hours, the mixture was subjected to centrifugation at $1,500 \times g$ for 10 minutes to recover a pellet. The pellet was redissolved gently in 5 ml of TES buffer and 2.0 ml of 1.5 mg/ml ethidium bromide was added. Then, cesium chloride was added to adjust the density of the mixture to 1.580. The solution was centrifuged at 18° C. at $105,000 \times g$ for 48 hours. After the density gradient centrifugation, a convalently-closed circular DNA was detected under UV irradiation as a high density band located in the lower part of the centrifugation tube. The band was taken out from the side of the tube with an injector to obtain a fraction containing pCG11 DNA. To remove ethidium bromide, the fraction was treated five times with an equal amount of cesium chloride saturated isopropyl alcohol solution consisting of 90% by volume isopropyl alcohol and 10% TES buffer solution. Then, the residue was dialysed against TES buffer solution.

(2) Cloning of the gene involved in the biosynthesis of histidine in *Corynebacterium glutamicum* C156:

In this step, 10 units of restriction enzyme BglII (product of Takara Shuzo Co.) was added to 200 µl of a BglII reaction solution (pH 7.5) consisting of 10 mM Tris, 7 mM $MgCl_2$, 60 mM NaCl and 7 mM 2-mercaptoethanol and containing 3 µg of pCG11 plasmid DNA and 9 µg of the chromosomal DNA prepared as above. The mixture was allowed to react at 37° C. for 60 minutes and heated at 65° C. for 10 minutes to stop the reaction. 40 µl of a T4 ligase buffer solution (pH 7.6) consisting of 200 mM Tris, 66 mM $MgCl_2$ and 100 mM dithiothreitol, 40µl of 5 mM ATP, 0.3 L µl of T4 ligase 1 (product of Takara Shuzo Co., 1 unit/µl) and 120 µl of $H_2O$ were added. The mixture was allowed to react at 12° C. for 16 hours and then used to transform *Corynebacterium glutamicum* LH33 which requires histidine and is sensitive to lysozyme.

The transformation was carried out using the protoplast of LH33 strain. The seed culture of LH33 was inoculated into NB medium and culturing was carried out with shaking at 30° C. Cells were harvested at an OD value of 0.6. The cells were suspended at about $10^9$ cells/ml in RCGP medium (pH 7.6)[consisting of 5 g/l glucose, 5 g/l casamino acid, 2.5 g/l yeast extract, 3.5 g/l $K_2HPO_4$, 1.5 g/l $KH_{2L\ PO4}$, 0.41 g/l $MgCl_2.6H_2O$, 10 mg/l $FeSO_4.7H_2O$, 2 mg/l $MnSO_4.(4-6)H_2O$, 0.9 mg/l $ZnSO_4.7H_2O$, 0.04 mg/l $(NH_4)_6Mo_7O_{24}.4H_2O$, 30

μg/l biotin, 2 mg/l thiamine hydrochloride, 135 g/l sodium succinate and 30 g/l polyvinyl pyrrolidone with a molecular weight of 10,000] containing 1 mg/ml lysozyme. The suspension was put in an L-tube and stirred slowly at 30° C. for 5 hours to obtain protoplasts.

Then, 0.5 ml of the protoplast suspension was put in a small test tube and centrifuged at 2,500×g for 5 minutes. The protoplasts were resuspended in 1 ml of TSMC buffer (pH 7.5) consisting of 10 mM magnesium chloride, 30 mM calcium chloride, 50 mM Tris and 400 mM sucrose and again subjected to centrifugation and washing. The washed protoplasts were resuspended in 0.1 ml of TSMC buffer solution. 100 μl of a mixture (1:1 by volume) of a two-fold concentrated TSMC buffer and the ligated DNA mixture described above was added to the protoplast suspension. Then, 0.8 ml of a solution containing 20% PEG 6,000 in TSMC buffer solution was added to the mixture. After 3 minutes, 2 ml of RCGP medium (pH 7.2) was added and the mixture was centrifuged at 2,500×g for five minutes. The supernatant fluid was removed and the protoplasts were suspended in 1 ml of RCGP medium. Then, 0.2 ml of the suspension was spread on RCGP agar medium (pH 7.2) containing 400 μg/ml spectinomycin and 1.4% agar and incubated at 30° C. for 7 days.

All the colonies formed on the agar medium were scraped, washed with physiological saline solution and centrifuged two times. The cells were spread on a minimal agar medium M1 (pH 7.2) consisting of 10 g/l glucose, 1 g/l $NH_4H_2PO_4$, 0.2 g/l KCl, 0.2 g/l $MgSO_4.7H_2O$, 10 mg/l $FeSO_4.7H_2O$, 0.2 mg/l $MnSO_4.(4-6)H_2O$, 0.9 mg/l $ZnSO_4.7H_2O$, 0.4 mg/l $CuSO_4.5H_2O$, 0.09 mg/l $Na_2B_4O_7.10H_2O$, 0.04 mg/l $(NH_4)_6Mo_7O_{24}.4H_2O$, 50 μg/l biotin, 2.5 mg/l p-aminobenzoic acid, 1 mg/l thiamine hydrochloride and 16 g/l agar and containing 100 μg/ml spectinomycin and incubated at 30° C. for 2 days. The transformants which are resistant to spectinomycin and do not require histidine were obtained from the colonies formed.

A plasmid DNA was isolated from cells of one of the transformants by the same ethidium bromide-cesium chloride density gradient centrifugation method as in step (1) above. The plasmid DNA was digested with restriction endonucleases and analyzed by agarose gel electrophoresis to determine the cleavage pattern of the plasmid DNA. The plasmid was named pPH8. pPH8 has the structure wherein about 10.6 Kb of a DNA fragment is inserted into the BglII site of pCG11.

H33 strain which is the parent of LH33 strain (FERM P-6909) requiring histidine and resistant to lysozyme was retransformed with pPH8 DNA. All of the transformants selected for spectinomycin-resistance simultaneously became histidine prototroph.

Therefore, it is certain that a gene involved in the biosynthesis of histidine-producing Corynebacterium glutamicum C156 was cloned in the plasmid. The cloning of the gene involved in the biosynthesis of histidine can be also carried out using H33 strain as a host from the beginning.

(3) Production of L-histidine by Corynebacterium glutamicum carrying pPH8:

Corynebacterium glutamicum LA-103 (FERM P-5947, ATCC 31866) was transformed with pPH8 DNA and a spectinomycin-resistant transformant was selected on RCGP agar medium containing 400 μg/ml spectinomycin. The transformant could grow on a minimal agar medium containing 3 g/ml 2-thoazole alanine. After the transformant was purified, the plasmid was isolated and its structure was analysed as mentioned above to confirm that the plasmid has the same structure as that of pPH8. A strain having pPH8, Corynebacterium glutamicum LA103/pPH8 has been deposited with the American Type Culture Collection, U.S.A. as Corynebacterium glutamicum K32 ATCC 39281.

Corynebacterium glutamicum LA103/pCG11 (ATCC 39022) and LA103/pPH8 (ATCC 39281) were tested for L-histidine production as follows.

A loopful of cells cultured in NB agar medium was inoculated in 5 ml of a production medium P5 adjusted to pH 7.4 with ammonia consisting of 12% molasses as sugar, 0.2 $KH_2PO_4$, 0.1% $K_2HPO_4$, 0.05% $MgSO_4.7H_2O$, 0.25% NaCl, 2.3% $(NH_4)_2SO_4$, 0.2% urea and 2% $CaCO_3$. Culturing was carried out at 30° C. for 75 hours. The amount of L-histidine formed was determined by a colorimetric method using sulfanilic acid (Pauly) reagent [H. Pauly, Hoppe-Seylers; Z. Physiolo. Chem., 42, 508 (1904), ibid 94, 284 (1915)]. The results are shown in Table 1.

TABLE 1

| Strain | Amount of L-histidine (mg/ml) |
|---|---|
| LA103/pCG11 | 0 |
| LA103/pPH8 (K32) | 2.6 |

(4) Production of L-histidine by pPH8 containing-strains, Corynebacterium herculis, Brevibacterium flavum and Brevibacterium lactofermentum:

In order to introduce plasmid pPH8 into Corynebacterium herculis ATCC 13868, Brevibacterium flavum ATCC 14067 and Brevibacterium lactofermentum ATCC 13869, these strains were transformed as follows.

Each strain was grown in SSM medium and penicillin G was added at an $OD_{660}$ value of 0.2 to a concentration of 0.3 unit/ml. Culturing was continued to an $OD_{660}$ value of 0.6. Cells were harvested and converted to protoplasts in RCGP medium containing 1 mg/ml lysozyme as mentioned above. Transformation was carried out using pPH8 as mentioned above and colonies formed on RCGP agar medium containing 400 μg/ml spectinomycin were selected as transformants.

Plasmid DNAs were prepared from the cells of the spectinomycin-resistant transformants according to the method described in Japanese Published Unexamined Patent Application Nos. 183799/82 and 134500/82. It was confirmed from the cleavage pattern that these plasmid DNAs have the same structure as that of pPH8. Therefore, it is certain that plasmid pPH8 which is a derivative of plasmid pCG11 is autonomously replicable in Corynebacterium herculis, Brevibacterium flavum and Brevibacterium lactofermentum and that plasmid pCG11 is broadly useful among these bacteria.

pPH8 containing-strains, Corynebacterium herculis K33, Brevibacterium flavum K34 and Brevibacterium lactofermentum K35 have been deposited with the American Type Culture Collection under ATCC 39282, 39283 and 39284.

These strains were tested for L-histidine production as follows.

One loopful of cells of each of pPH8 containing-strains as well as parent strains thereof cultured in NB agar medium was inoculated in 5 ml of a production medium P5. Culturing was carried out with shaking at 30° C. for 75 hours. The amount of L-histidine formed was determined by the colorimetric method of Pauly. The results are shown in Table 2.

TABLE 2

| Strain | Amount of L-histidine (mg/ml) |
|---|---|
| ATCC 13868 | 0 |
| ATCC 13868/pPH8 (K33, ATCC 39282) | 2.4 |
| ATCC 14067 | 0 |
| ATCC 14067/pPH8 (K34, ATCC 39283) | 3.0 |
| ATCC 13869 | 0 |
| ATCC 13869/pPH8 (K35, ATCC 39284) | 2.0 |

As is apparent from the above results, a gene involved in the biosynthesis of histidine derived from *Corynebacterium glutamicum* is expressed and contribute to the production of histidine in *Corynebacterium herculis*, *Brevibacterium flavum* and *Brevibacterium lactofermentum*.

EXAMPLE 2

Construction of the combinant plasmid containing a gene involved in L-histidine biosynthesis of *Escherichia coli* (*E.coli*) K-12 ATCC 23740, conferring 1,2,4-triazole-3-alanine -resistance to the plasmid by mutation and the production of L-histidine by a strain of *Corynebacterium glutamicum* harbouring the resistant plasmid.

(1) Preparation of chromosomal DNA of *E.coli* K-12 ATCC23740 and plasmid pCE53

The chromosomal DNA was prepared from a histidine prototrophic strain of *E.coli* K-12 ATCC23740 by the phenol method of Smith (Methods in Enzymology 12 Part A p545 1967). The vector plasmid, pCE53 was prepared according to the method of An (An. G., et al. J. Bacteriol. 140 400 1979.) from *E.coli* K-12 MM294 carrying pCE53 (MM294/pCE53).

It was constructed by transforming MM294 (Müller-Hill, B. et al., in Protein Ligand Interactions, eds. Sund, H. and Blauer, G. p211 1975). with plasmid pCE53 isolated from *Corynebacterium glutamicum* (*C.glutamicum*) LA103/pCE53 according to the method described above. The preparation of competent cells of MM294 and transformation were done as described in the next section. Kanamycin resistant (Km$^r$) transformants were selected on L agar medium (1% Tryptone, 0.5% yeast extract, 0.5% NaCl, 0.1% glucose and 1.6% agar, pH adjusted to 7.2) containing 25 μg/ml kanamycin. Plasmid DNA was prepared from one of the transformants by the method of An et al. The structure of the plasmid was analyzed by digesting with restriction endonucleases and was found to be the same as that of pCE53.

*C.glutamicum* LA103 carrying pCE53 was constructed as follows. The Bgl II-restricted pCG1 and Bam HI partially-digested pGA22 were ligated with T4 L DNA ligase (product of Takarashuzo Co.). *C.glutamicum* LA103 was transformed with the ligation mixture as described in the Japanese Published Unexamined Patent Application Nos. 186492/82 and 186489/82. Km$^r$ transformants were selected on RCGP agar medium containing 200 μg/ml kanamycin. Plasmids were isolated from these transformants and their structures were analyzed. A plasmid from one of the transformants contains pCG1 inserted in the Bam HI site near the Km gene of pGA22. It was designated as pCE53.

(2) Cloning of a gene involved in histidine biosynthesis from *E.coli* K-12 ATCC23740.

To 200 μl of a restriction enzyme PstI buffer [20 mM Tris-HCl (pH 7.5), 10 mM MgCl$_2$, 50 mM (NH$_4$)$_2$SO$_4$, 0.01% bovine serum albumin] containing 3 μg of pCE53 and 9 μg of the chromsomal DNA of *E.coli* K-12 ATCC 23740 prepared as described above, 10 units of PstI (Takarashuzo Co.) was added. The mixture was incubated at 37° C. for 60 min and then the reaction was stopped by heating at 65° C. for 10 min. To the digestion mixture, 40 μl of T4 ligase buffer I was added together with 40 μl of 5 mM ATP, 0.3 unit of T4 ligase and 120 μl water and the mixture was incubated at 12° C. for 16 hr. The ligation mixture was used to transform *E.coli* K-12 JC411 (hisG, leuB, argG, metB; Clark et al., Molec. Gen. Genet. 105 1 1969). The competent cells of JC411 were prepared according to the method of Dagert et al (Gene 6:23 1979). The cells were grown in L medium to the middle of logarithmtic phase of growth at 37° C. with shaking. After the culture was kept in ice for 10 min, cells were harvested by centrifugation and suspended in 20 ml of cold 0.1M CaCl$_2$. The suspension was kept in ice for 20 min and then cells were harvested and suspended in 0.5 ml cold 0.1M CaCl$_2$ and kept at 0° C. for 18 hr.

A portion (50 μl) of the ligation mixture was added to 150 μl of the CaCl$_2$-treated cell suspension described above. After the mixture was kept at 0° C. for 10 min, it was incubated at 37° C. for 3 min. Two ml of L medium was added to the mixture and cells were grown at 37° C. for 2 hr with shaking. After washing with a saline twice by centrifugation, cells were plated and grown on A agar medium (Na$_2$HPO$_4$ 8 g, KH$_2$PO$_4$ 2 g, (NH$_4$)$_2$SO$_4$ 1 g, MgSO$_4$.7H$_2$O 0.1 g, thiamine.HCl 4 mg, glucose 10 g and agar 16 g in 1 liter water, pH adjusted to 7.2) containing 50 μg of leucine, arginine and methionine and 25 μg kanamycin per ml. Plasmids were isolated from the transformants as described above and their structures were analyzed by digesting with restriction endonuleases and agarose gel electrophoresis. A plasmid from one of the transformants, designated as pEG7, has a 4.8 kb (kilobase pairs) PstI fragment in the unique PstI site of pCE53.

pEG7 isolated from this transformant was used to retransform the competent cells of JC411 prepared as described above. All the transformants grown on NB agar medium containing 25 μg/ml kanamycin were found histidine prototrophs. Thus it is clear that plasmid pEG7 can complement hisG mutation of JC411.

(3) Introduction of pEG7 into *C.glutamicum*.

*C.glutamicum* LA 103 (lysozyme-sensitive, arg, met) was transformed with pEG7 by the protoplast transformation method described in Example 1(2). Transformants grown on RCGP agar medium containing 200 μg/ml kanamycin had a plasmid same to the plasmid pEG7 as judged from the digestion pattern with restriction endonuleases.

(4) Conferring resistance to a histidine analogue, 1,2,4-triazole-3-alanine (TRA).

*C.glutamicum* LA103 carrying pEG7 was mutagenized with nitroso guanidine by a conventional method and plated on minimal agar medium M1 containing 1 mg/ml TRA, 50 μg/ml arginine and methionine. After incubation at 30° C. for 5 days, colonies formed were scraped and suspended in a saline. The cell suspension was inoculated into NB medium containing 25 μg/ml kanamycin at a cell density of 10$^7$/ml and incubated at 30° C. over night with shaking. Plasmids were isolated from the cultured cells as described above (Example 1(1)). The mixture of plasmids isolated were used to re-transform *C.glutamicum* LA103. A plasmid was isolated from one of Km$^r$ transformants which also acquired TRA-resistance. The plasmid has the same digestion pattern with restriction endonuleases as that of pEG7. It was designated pEG7t180.

(5) Subcloning of the 4.8 kb PstI DNA fragment of pEG7t180.

To conform the presence of TRA$^r$ mutation on the 4.8 kb PstI fragment derived from E.coli, it was subcloned as follows. Each 3 μg of pEG7t180 and pCG11 (Example 1) were digested with PstI and ligated as described above. The ligation mixture was used to transform C.glutamicum LA103 as described in Example 1(2). Transformants were selected on RCGP medium containing 400 μg/ml spectinomycin (Spc). Spc-resistant transformants obtained were plated on A agar medium containing 1 mg/ml TRA, 50 μg/ml arginine and methionine, NB agar medium containing 25 μg/ml kanamycin and NB medium containing 100 μg/ml spectinomycin. After incubation at 30° C. for 5 days, a strain which was Spc and TRA-resistant and Km-sensitive was selected and purified. A plasmid was isolated from the cultured cells of the strain and analyzed by digestion with restriction endonuleases. The plasmid contains the 4.8 kb Pst fragment inserted at the unique PstI site of pCG11 (designated pCSt180).

Production tests of C.glutamicum LA103 carrying pCG11 (ATCC39022), pEG7, pEG7t180, and pCSt180 were done using production medium P5 supplemented with 200 μg/ml arginine and methionine. Histidine accumulated after cultivation at 30° C. for 75 hrs was measured colorimetrically as described in Example 1(3). The result is shown in Table 3.

TABLE 3

| Strain used | Histidine accumulated (mg/ml) |
|---|---|
| LA103/pEG7 | 0 |
| LA103/pEG7t180 | 1.8 |
| LA103/pCG11 | 0 |
| LA103/pCSt180 (K-49) | 2.0 |

These results indicate that the TRA$^r$ mutation resides on the 4.8 kb PstI fragment derived from the chromosomal DNA of E.coli K-12, and that the production of histidine by C.glutamicum LA103 carrying pEG7t180 or pCSt180 was due to the expression of the gene(s) on the fragment which is responsible for the TRA-resistance.

Strain K-49 has been deposited with Fermentation Research Institute, Agency of Industrial Science and Technology, Ibaraki, Japen, under the accession number FERM BP-464.

What is claimed is:

1. A process for producing histidine, which comprises:
    transforming a host microorganism belonging to the genus Corynebacterium or Brevibacterium with a vector containing a DNA fragment containing a gene isolated from *Corynebacterium glutamicum* or *Escherichia coli* coding for ATP phosphoribosyl transferase; culturing the transformant in a nutrient medium; accumulating histidine in the culture medium; and recovering histidine therefrom.

2. The process according to claim 1, wherein the DNA fragment can confer a microorganism resistance to the group consisting of histidine and a histidine analog.

3. The process according to claim 1, wherein the DNA fragment codes for an enzyme resistant to the group consisting of histidine and a histidine analog.

4. The process according to claim 1, wherein the host microorganism is selected from the group consisting of the species *Corynebacterium glutamicum, Corynebacterium herculis, Brevibacterium flavum* and *Brevibacterium lactofermentum.*

5. The process according to claim 1, wherein the host microorganism belongs to the genus Corynebacterium or Brevibacterium and is sensitive to lysozyme.

6. The method according to claim 5, wherein the host microorganism is *Corynebacterium glutamicum* L-22.

7. A microorganism belonging to the genus Corynebacterium or Brevibacterium containing a vector containing a DNA fragment containing a gene isolated from *Corynbacterium glutamicum* or *Escherichia coli* coding for ATP phosphoribosyl transferase.

8. A biologically pure culture of *Corynebacterium glutamicum* K32, ATCC 39281, *Corynebacterium herculis* K33, ATCC 39282, *Brevibacterium flavum* K34, ATCC 39283, or *Brevibacterium lactofermentum* K35, ATCC 39284.

9. A biologically pure culture of *Corynebacterium glutamicum* K49, FERM BP-464.

* * * * *

UNITED STATES PATENT AND TRADEMARK OFFICE
CERTIFICATE OF CORRECTION

PATENT NO. : 4,927,758
DATED : May 22, 1990
INVENTOR(S) : TORU MIZUKAMI ET AL.

It is certified that error appears in the above-identified patent and that said Letters Patent is hereby corrected as shown below: TITLE PAGE

AT [56] REFERENCES CITED

Foregin Patent Documents,
"01311171 1/85 European Pat. Off. ." should read
--0131171 1/85 European Pat. Off. .--.

COLUMN 1

Line 9, "histindine" should read --histidine--.

COLUMN 2

Line 38, "183799/82), pCE54," should read
--183799/82), pCE53, pCE54,--.
Line 57, "descrived" should read --described--.

COLUMN 3

Line 6, "Nos. 186493/82" should read --Nos. 186492/82--.

COLUMN 5

Line 17, "0.4 mg.1 $CuSO_4 \cdot 5H_2O$," should read
--0.4 mg/1 $CuSO_4 \cdot 5H_2O$,--.

Line 18, "0.04 mg/1 $(NH_4)_6Mo_7O_{24} \cdot 4H_2)$," should read
--0.04 mg/1 $(NH_4)_6Mo_7O_{24} \cdot 4H_2O$,--.

Line 40, "polyvinyl purrolidone." should read
--polyvinyl pyrrolidone.--.

COLUMN 7

Line 17, "asked" should read --added--.

UNITED STATES PATENT AND TRADEMARK OFFICE
CERTIFICATE OF CORRECTION

PATENT NO. : 4,927,758

DATED : May 22, 1990

INVENTOR(S) : TORU MIZUKAMI ET AL.

It is certified that error appears in the above-identified patent and that said Letters Patent is hereby corrected as shown below:

COLUMN 8

Line 53, "0.3 L µl" should read --0.3 µl--.
Line 66, "1.5 g/l $KH_{2LPO4}$," should read --1.5 g/l $KH_2PO_4$,--.

COLUMN 9

Line 67, "2-thoazole alanine." should read --2-thiazole alanine.--.

COLUMN 11

Line 55, "L" should be deleted.

COLUMN 14

Line 39, Italics should be deleted.

Signed and Sealed this

Twenty-first Day of April, 1992

Attest:

HARRY F. MANBECK, JR.

Attesting Officer — Commissioner of Patents and Trademarks